(12) United States Patent
Wang et al.

(10) Patent No.: US 7,289,221 B2
(45) Date of Patent: Oct. 30, 2007

(54) MACH ZEHNDER PHOTONIC CRYSTAL SENSORS AND METHODS

(75) Inventors: Shih-Yuan Wang, Palo Alto, CA (US); M. Saif Islam, Mountain View, CA (US); Alex Bratkovski, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 415 days.

(21) Appl. No.: 10/951,918

(22) Filed: Sep. 27, 2004

(65) Prior Publication Data

US 2006/0066866 A1 Mar. 30, 2006

(51) Int. Cl.
*G01B 9/02* (2006.01)
*G02B 6/00* (2006.01)

(52) U.S. Cl. .......................................... 356/477; 385/12
(58) Field of Classification Search ........ 356/477–479, 356/481, 450; 385/12–14
See application file for complete search history.

(56) References Cited

U.S. PATENT DOCUMENTS

| 5,004,914 | A | 4/1991 | Vali et al. | |
|---|---|---|---|---|
| 6,175,671 | B1 | 1/2001 | Roberts | |
| 6,493,090 | B1* | 12/2002 | Lading et al. | 356/484 |
| 6,542,682 | B2 | 4/2003 | Cotteverte et al. | |
| 6,640,034 | B1* | 10/2003 | Charlton et al. | 385/122 |
| 6,658,173 | B2* | 12/2003 | Delwala | 385/15 |
| 6,674,949 | B2 | 1/2004 | Allan et al. | |
| 6,917,431 | B2* | 7/2005 | Soljacic et al. | 356/477 |
| 6,956,651 | B2* | 10/2005 | Lackritz et al. | 356/445 |
| 7,068,865 | B2* | 6/2006 | Hamann et al. | 385/8 |
| 2002/0018504 | A1 | 2/2002 | Coldren | |
| 2002/0164118 | A1 | 11/2002 | Paddon et al. | |
| 2003/0011775 | A1 | 1/2003 | Sofacic et al. | |
| 2003/0161565 | A1* | 8/2003 | Bastian | 385/3 |
| 2005/0084213 | A1* | 4/2005 | Hamann et al. | 385/40 |
| 2005/0287696 | A1* | 12/2005 | Dumais et al. | 438/69 |
| 2006/0024013 | A1* | 2/2006 | Magnusson et al. | 385/129 |
| 2006/0034577 | A1* | 2/2006 | Furuya et al. | 385/129 |
| 2006/0066866 | A1* | 3/2006 | Wang et al. | 356/481 |
| 2006/0066867 | A1* | 3/2006 | Beausoleil | 356/481 |
| 2006/0072642 | A1* | 4/2006 | Wang et al. | 372/50.1 |
| 2006/0140567 | A1* | 6/2006 | Kittaka et al. | 385/129 |

OTHER PUBLICATIONS

G. Labeyrie, A. Landragin, J. v. Zanthier, R. Kaiser, N. Vanstennkiste, C. I. Westbrook, A. Aspect, "Detailed study of a high-finesse planar waveguide for evanescent wave atomic mirrors," Quantum Semiclass Opt. 8 603-627 (Feb. 1996).

T.D. Happ, M. Kamp and A. Forchel, "Ridge waveguide lasers with 2D photonic crystal mirrors," Inst. Phys. Conf. Ser., No. 166: Chapter 6, Proceedings of the 26th Int. Sym. Compound Semiconductors, Berlin (Germany), Aug. 22-26, 1999, pp. 411-414, 2000.

(Continued)

*Primary Examiner*—Patrick Connolly

(57) ABSTRACT

A sensor apparatus includes a photonic crystal structure including a Mach Zehnder interferometer with a reference arm and a sensor arm configured to provide an evanescent field through a sensed medium region adjacent to the sensor arm.

21 Claims, 5 Drawing Sheets

OTHER PUBLICATIONS

"Sensor industry learns lessons from telecoms," Opto & Laser Europe (Nov. 2001).

Yong Hee Lee and Han Youl Ryu, "Custom crystals control photons," IEEE Circuits and Devices Magazine, May 2002, 18(3):8-15.

M. Ohtsu, K. Kobayashi, T. Kawazoe, S. Sangu, and T. Yatsui, "Nanophotonics: Design, Fabrication, and Operation of Nanometric Devices Using Optical Near Fields," IEEE J. Selected Topics in Quantum Electron, vol. 8, No. 4, pp. 839-862 (Jul. 2002).

S. W. Leonard, H. M. van Driel, J. Schilling and R. B. Wehrspohn, "Ultrafast band-edge tuning of a two-dimensional silicon photonic crystal via free-carrier injection", Physics Review B 66, 161102 (Oct. 2002).

M. Loncar, T. Yoshie, J. Vuckovic, A. Scherer, H. Chen, D. Deppe, P. Gogna, Y. Qiu, D. Nedeljkovic and T. P. Pearsall, "Nanophotonics based on planar photonic crystals," IEEE LEOS Annual Meeting, Glasgow, Scotland, Nov. 2002.

GP Nordin, S. Kim, J. Cai, and J. Jiang, "Hybrid integration of conventional waveguide and photonic crystal structures," Optics Express, vol. 10 Issue 23 p. 1334 (Nov. 2002).

Sharkawy, Ahmed; Shi, Shouyuan; Prather, Dennis W., "Heterostructure photonic crystals: theory and applications," Applied Optics, vol. 41, No. 34, p. 7245-7253 (Dec. 2002).

A. Scherer, T. Yoshie, M. Loncar, J. Vuckovic, K. Okamoto, D. Deppe, "Photonic crystal nanocavities for efficient light confinement and emission," (invited) J. Korean. Phys. Soc., 42, pp. S768-S773 (Feb. 2003).

Thomas F. Krauss, "Planar photonic crystal waveguide devices for integrated optics," Phys. Stat. Sol. 197, 688-702 (Jun. 2003).

Thomas F. Krauss, PICCO Final Report (Sep. 2003).

Chad S. Wang, Daniel Cohen, Jill A. Nolde, Dan D. Lofgreen, and Larry A. Coldren, "A Diode Laser Chemical Sensor Utilizing an Oxidized Lower Cladding Layer for High Sensitivity," Proc. LEOS 2003, paper No. ThY7, pp. 989-990, Tucson, Arizona (Oct. 2003).

Alejandro Martinez, Jaime Garcia, Guillermo Sanchez, Javier Marti, "Planar photonic crystal structure with inherently single-mode waveguides," J. Opt. Soc. Am. A., vol. 20 Issue 11 pp. 2131-2136 (Nov. 2003).

Barclay PE, Srinivasan K, Painter O, "Design of photonic crystal waveguides for evanescent coupling to optical fiber tapers and for integration with high-Q cavities," J. Opt. Soc. Am. B., vol. 20 Issue 11 pp. 2274-2284 (Nov. 2003).

Sharee J. McNab, Nikolaj Moll, and Yurii A. Vlasov, "Ultra-low loss photonic integrated circuit with membrane-type photonic crystal waveguides," Optics Express, vol. 11, No. 22, pp. 2927-2939 (Nov. 2003).

Olivier, S.; Weisbuch, C.; Benisty, H., "Compact and fault-tolerant photonic crystal add-drop filter," Optics Letters, vol. 28, No. 22, pp. 2246-2248 (Nov. 2003).

Micro and Nanotechnology Laboratory, "Task II: Development of an Integrated Guided-Wave Interferometer-Based Bio-Sensor System," downloaded Apr. 8, 2004, http://www.micro.uiuc.edu/boss/TaskII.html.

Lading et al—"Comparing Biosensors"—Proc of IEEE Int'l Conf on Sensors—vol. 1 of 2—conf 1—Jun. 12, 2002.

Patent Abstracts of Japan—NEC Corp—"Photonic Crystal Optical Functional Element"—vol. 2003 No. 12—Dec. 15, 2003.

Kinrot N—"Analysis of Bulk Material Sensing Using a Periodically Segmented Waveguide Mach-Zender Interferometer for Biosensing"—Journal of Lightwave Technology vol. 22/No. 10.

Camargo E A et al.—Mach-Zehnder Cahnnel-Guide Device Structure Based on 2D Photonic Crystal—Proc of the SPIE—vol. 5450 No. 1—2004.

Patent Abstracts of Japan—Mitsui Chemicals—"Optical Modulator and Metod for Manufacturing the Same"—vol. 2003 No. 12—Dec. 15, 2003.

Asakawa K—"Fabrication and Characterization of Photonic Crystal Slab Waveguides and Application to Ultra-Fast All-Optical Switching Devices"—vol. 1—Jun. 29, 2003.

Lim J H et al—Mach-Zender Interferometer Formed in a Photonic Crystal Fiber Based on a Pair of Long-Period Fiber Gratings—Optics Letters—vol. 29 No. 4 Feb. 13, 2004.

Bock W J et al—"Fiber Optic Sensing Based on Photonic Crystal Holey Fibers"—Proc of the SPIE—vol. 5260 No. 1—2003.

* cited by examiner

MACH ZEHNDER PHOTONIC CRYSTAL SENSORS AND METHODS

CROSS-REFERENCE TO RELATED APPLICATIONS

This application is related to U.S. patent application Ser. No. 10/951,916 entitled "Photonic Crystal Laser Sensors and Methods" filed herewith.

TECHNICAL FIELD

The present invention relates generally to sensors, and, more particularly, to the use of photonic crystal waveguides in sensors.

BACKGROUND ART

One form of chemical detection device employs spectroscopic-based techniques. For example, such a device samples air by passing it through a filter having a surface coating adapted to adhere to the chemical vapors being detected. The filter traps molecules of the chemical vapor being detected and is then burned (i.e., vaporized) to produce a light spectrum indicative of the presence or absence of the chemical vapor being detected. A spectrometer is then employed to split the various wavelength components of the light spectrum due to the vaporization of the chemical vapor. The spectrometer produces a pattern of lines characteristic of the presence or absence of the chemical being detected. The mass spectroscopic-based systems available today, however, tend to be too large and require too much power to be field portable.

Another type of chemical detection device employs quartz crystals as mechanical oscillators. Such devices generally measure the change in frequency of an oscillating quartz crystal as it is affected by the mass of molecules which are being detected. The change in mass, however, of quartz crystal oscillators as they absorb chemical vapors, is so small that the change in their frequency of oscillation is also extremely small. This limits the sensitivity of quartz crystal-based detection devices and the number of different applications in which they can be reliably employed.

It would be useful to be able to provide a sensing technology that is highly sensitive, power efficient, and compact in size (e.g., nanometer scale).

DISCLOSURE OF INVENTION

According to an example embodiment, a sensor apparatus includes a photonic crystal structure including a Mach Zehnder interferometer with a reference arm and a sensor arm configured to provide an evanescent field through a sensed medium region adjacent to the sensor arm.

According to an example embodiment, a sensor apparatus includes multiple sensor elements, each of the sensor elements including a photonic crystal Mach Zehnder interferometer with a reference arm and a sensor arm configured to provide an evanescent field through a sensed medium region adjacent to the sensor arm, and a mechanism for detecting outputs of the multiple sensor elements and converting the outputs into data.

According to an example embodiment, a method for sensing includes providing a photonic crystal Mach Zehnder interferometer that generates an evanescent field through a sensed medium region, providing an article of medium at the sensed medium region, optically coupling a light source to an input of the photonic crystal Mach Zehnder interferometer, and detecting an output of the photonic crystal Mach Zehnder interferometer.

BEST MODES FOR CARRYING OUT THE INVENTION

Definitions

Micron-scale dimensions refers to dimensions that range from 1 micrometer to a few micrometers in size.

Sub-micron scale dimensions refers to dimensions that range from 1 micrometer down to 0.05 micrometers.

Nanometer scale dimensions refers to dimensions that range from 0.1 nanometers to 50 nanometers (0.05 micrometers).

PRESENT EMBODIMENTS

Various embodiments of the present invention pertain to interferometric and other detector structures that use photonic crystals for chemical, biological and/or other types of sensing with evanescent fields.

Figure 10:
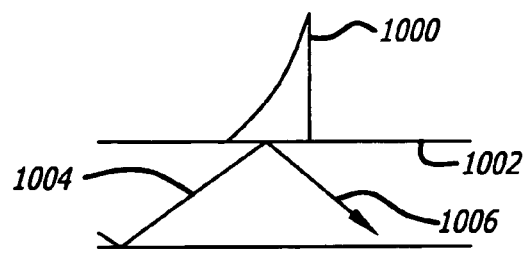
FIG. 10 illustrates an example evanescent field.

Evanescent fields are created by total internal reflection. FIG. 10 illustrates an example of an exponentially decaying evanescent field 1000 on the opposite side of a totally internally reflecting interface 1002 (e.g., a waveguide). When a medium of high refractive index is brought into the evanescent field, this frustrates the total internal reflection of the incident light 1004, changing the amplitude of the reflected light 1006. Sensors and sensing methods described herein exploit evanescent fields associated with photonic crystal structures.

Figure 1:
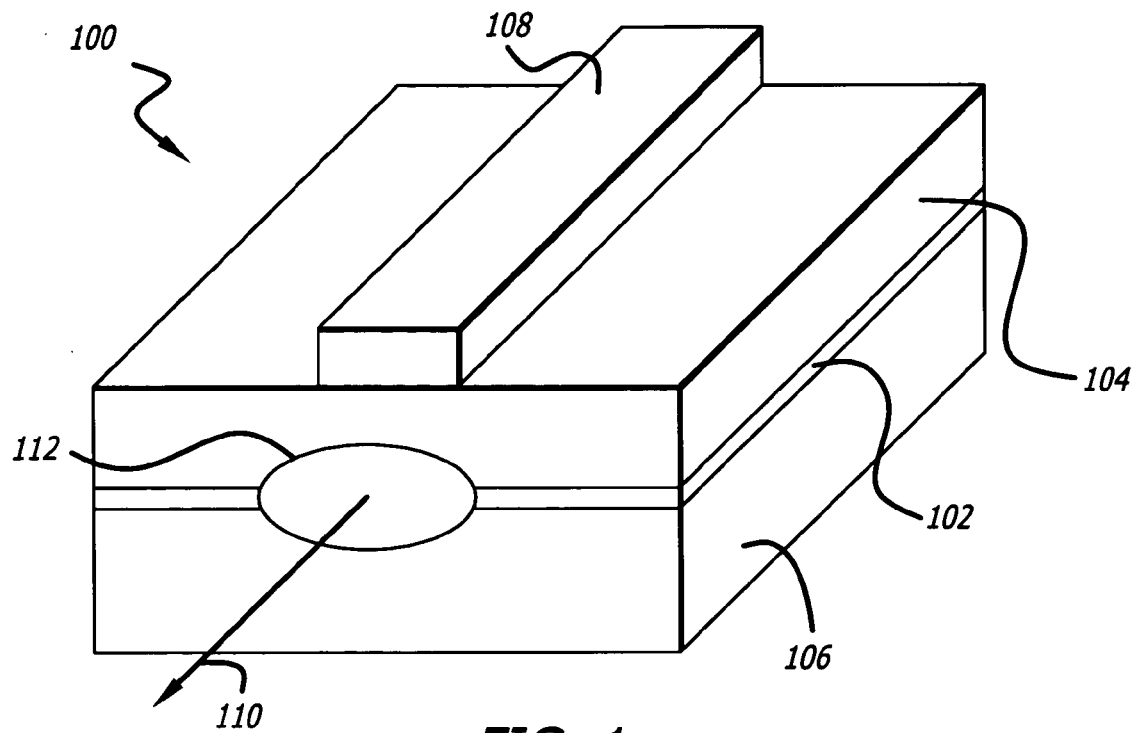
FIG. 1 illustrates a ridge semiconductor laser.
Figure 2:
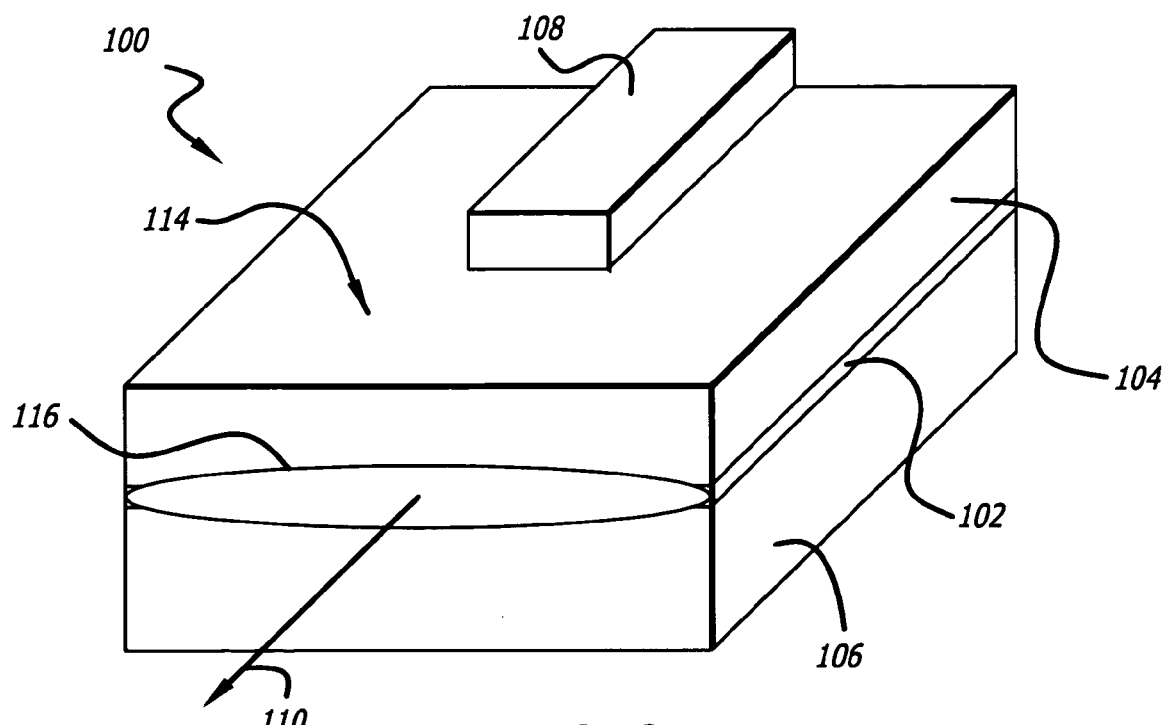
FIG. 2 illustrates partial removal of the ridge from the laser of FIG. 1 such that light is no longer being confined under the ridge and goes into a slab mode.
Figure 3:
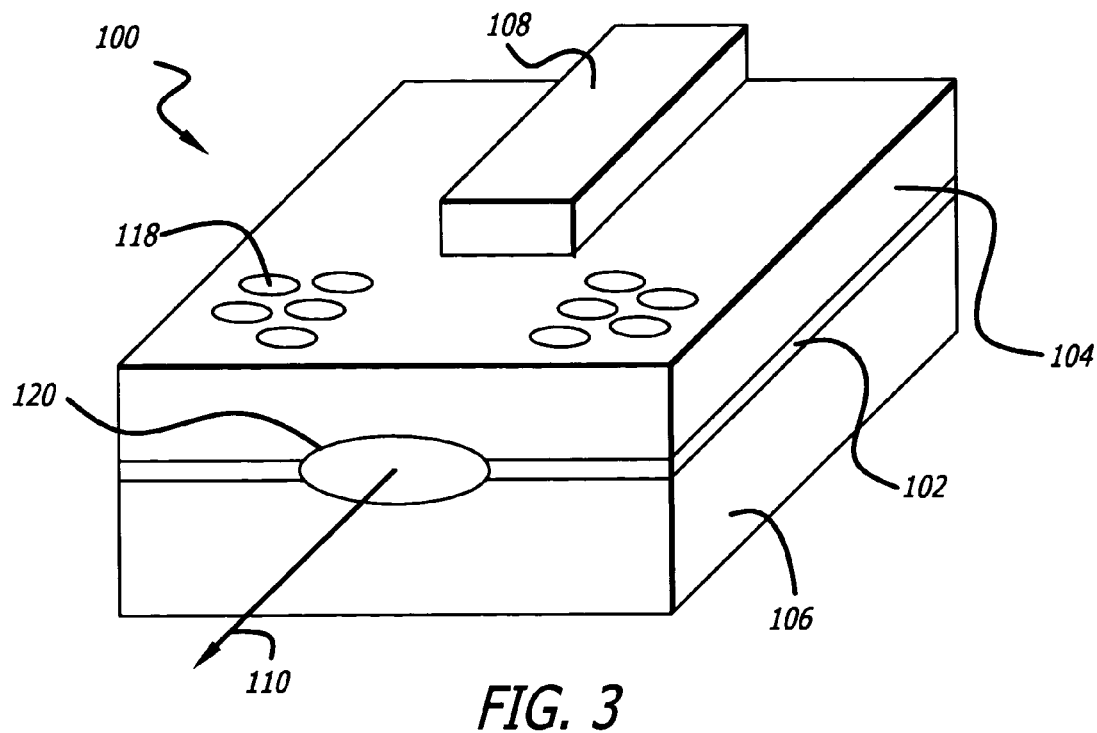
FIG. 3 illustrates the formation of photonic crystal voids on the semiconductor laser surface of FIG. 2 to guide the light.

Referring to FIG. 1, an example ridge semiconductor laser 100 formed as shown includes an active layer 102, an overclad layer 104, an underclad layer 106, and a ridge 108. Light output (along a direction denoted by arrow 110) from the ridge semiconductor laser 100 is guided by the ridge 108 as indicated by ellipse 112. According to various embodiments and referring to FIG. 2, the ridge semiconductor laser 100 is modified to partially remove the ridge 108 in region 114 as shown such that the light is no longer confined under the ridge 108 and goes into slab mode as indicated by ellipse 116. Next, and referring to FIG. 3, photonic crystal voids 118 are formed on the semiconductor laser surface such that the light is guided as indicated by ellipse 120, thereby providing a photonic crystal laser structure. In this example, the overclad layer 104 and the underclad layer 106 have refractive indices lower than that of the core layer 102, and all three layers are patterned with the photonic crystal structure. The photonic crystal structure defines a defect waveguide. An optical signal traveling in the defect waveguide is confined in the horizontal direction by the photonic crystal structure, and in the vertical direction by the lower refractive index cladding layers. Changes in parameters of the photonic crystal will affect the photonic bandgap of the photonic crystal, the band of allowed guided modes of the defect waveguide, and the propagation of an optical signal in the defect waveguide.

Figure 4A:
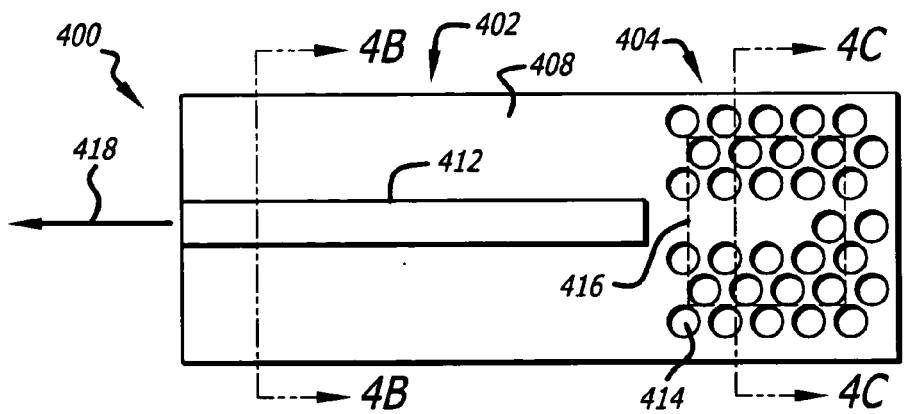
FIG. 4A is a top view of an example embodiment of a laser sensor apparatus with a photonic crystal mirror.
Figure 4B:
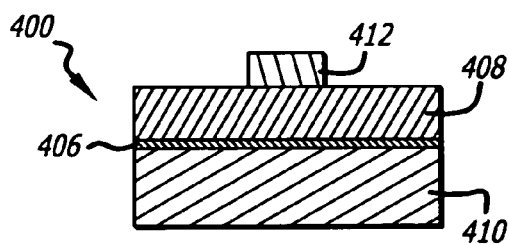
FIGS. 4B and 4C are cross-sectional views of the laser sensor apparatus with a photonic crystal mirror of FIG. 4A.
Figure 4C:
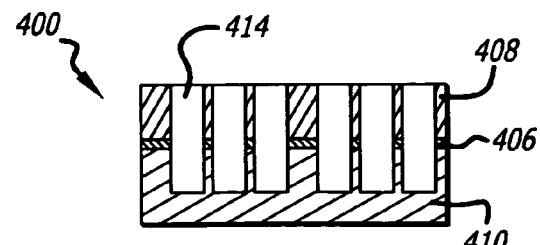

By way of example, and referring to FIGS. 4A-4C, such photonic crystal structures can be used to provide an evanescent field through a sensed medium region such that the photonic crystal structure functions as a cavity/resonator for the laser. In this example embodiment, a laser sensor apparatus 400 includes a laser 402 and a photonic crystal mirror structure 404 which is optically coupled to the laser 402 as shown. In this example, the laser 402 is a semiconductor laser that includes an active layer 406, an overclad layer 408, an underclad layer 410, and a ridge 412; however, it should be appreciated that the principles described herein are applicable to other light sources (e.g., fiber lasers). The photonic crystal mirror structure 404 in this example embodiment includes photonic crystal voids 414 formed in a pattern as shown through the overclad layer 408, the active layer 406, and the underclad layer 410. The photonic crystal mirror structure 404 is also provided with a sensed medium region 416 (shown in dashed lines) positioned over the photonic crystal waveguide defined by the voids 414. In operation, a chemical, biological or other medium is placed in the sensed medium region 416. The evanescent field resulting from light propagating along the photonic crystal structure "probes" the medium. More specifically, the evanescent tail of the mode propagating along the photonic crystal waveguide structure passes through the medium, and the resulting interactions with the medium can alter the propagation speed and/or attenuation of the evanescent tail. The thickness of the overclad layer 408 can also be adjusted to provide a receptacle for the medium, to accommodate the refractive indices of various combinations of core and cladding materials, etc. In this example embodiment, the voids 414 are arranged in a pattern that provides the photonic crystal mirror structure 404. Thus, interaction between the evanescent field and the medium in the sensed medium region 416 effects the characteristics of the light (denoted by arrow 418) reflected by the photonic crystal mirror structure 404, thereby providing an output indicative of the sensed medium.

With respect to materials, the photonic crystal structures (e.g., nanostructures and sub-micron structures) can be fabricated on III-V semiconductor materials (e.g., GaAs or InP and their alloys). Molecular beam epitaxy (MBE) can be used to fabricate very thin layers for the III-V semiconductors with a very accurate control during epitaxial growth.

Other materials can be used to fabricate the planar photonic crystal waveguides described herein. Generally, the bulk materials can be any material substantially transparent to the wavelengths of the optical signal. For example, the planar photonic crystal bulk material can be doped silica, undoped silica, silicon, a polymeric organic material, an organic/inorganic hybrid material, an inorganic glass (e.g., chalcogenide glass), or any other suitable materials. The difference in refractive index between the core and the cladding layers can be achieved by using two substantially different materials, or by selectively doping similar materials, or by other methods known to those skilled in the art. The voids can be filled with air, or with another material. In various embodiments, the material of the voids has a refractive index that is substantially different than the bulk photonic crystal material. The geometry of the pattern of voids (more generally, the "photonic crystal structures") can be hexagonal, square, triangular, rectangular, or otherwise, depending on the in-plane photonic band gap desired. Moreover, the voids can be formed with shapes other than cylindrical.

The photonic crystal structures described herein can be fabricated in a variety of different ways. Nanoimprinting, a technique using nanoscale to sub micron and micron scale patterns to stamp or print designs on chip surfaces, can be used. By way of example, a nanoimprinting technique can involve using a hard mold to create nanoscale features by directly imprinting into a polymer film. After a pattern has been imprinted, the photonic crystal defects are created by etching the pattern (e.g., anisotropic dry etching with reactive ions).

Other photonic crystal structure fabrication techniques can be employed. For example, Focused Ion Beam (FIB) can be used to drill the photonic crystal holes. To address any damage to optical/electrical quality caused by FIB, additional optical pumping and/or electrical can be provided on the photonic crystal part to recover losses. Ultraviolet (UV) laser lithography, laser interference lithography, and electron-beam lithography can also be used.

Figure 5:
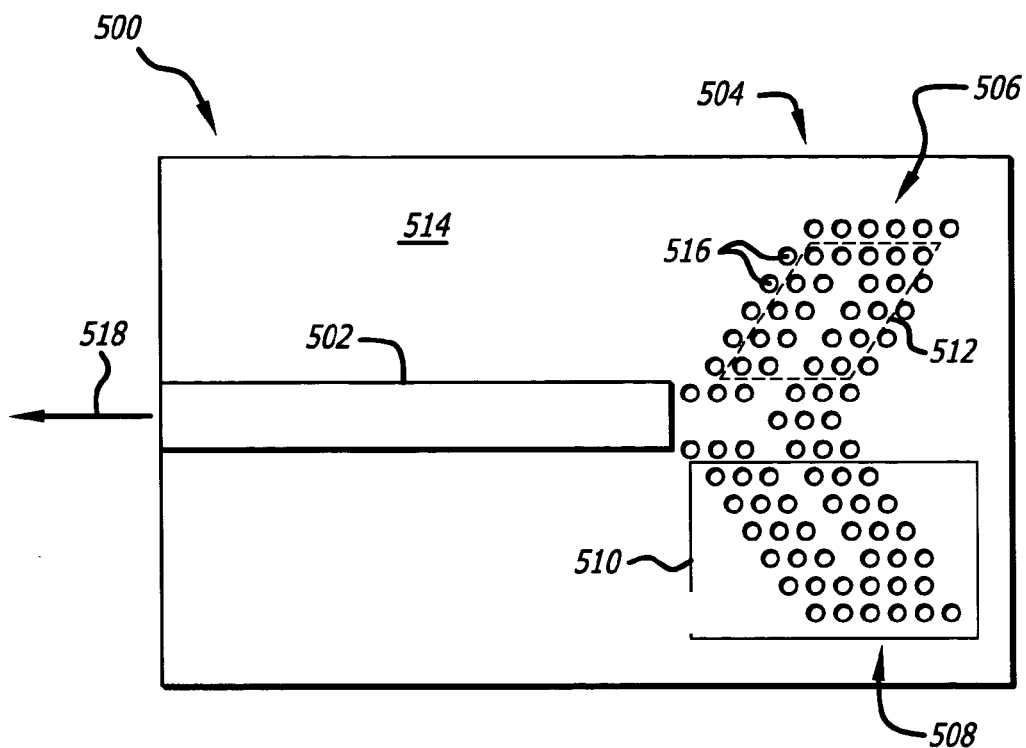
FIG. 5 is a top view of an example laser sensor apparatus with a photonic crystal double pass interferometer that includes a sensor arm and a passivated reference arm.

Photonic crystal mirrors can be used singly or, as described below, in an interferometric arrangement in a sensor apparatus. By way of example, and referring to FIG. 5, a laser sensor apparatus 500 includes a laser 502 (e.g., a semiconductor laser) and a photonic crystal double pass interferometer structure 504 which is optically coupled to the laser 502 as shown. In this example, the photonic crystal double pass interferometer structure 504 includes a sensor arm 506 and a reference arm 508 in a Y-configuration as shown. At the end of each arm, a photonic crystal mirror is provided. In this example, the reference arm 508 is passivated, as indicated by passivation region 510. The photonic crystal double pass interferometer structure 504 is also provided with a sensed medium region 512 (shown in dashed lines) positioned over the photonic crystal waveguide of the sensor arm 506. In operation, a chemical, biological or other medium is placed in the sensed medium region 512. The evanescent field resulting from light propagating along the photonic crystal structure "probes" the medium. More specifically, the evanescent tail of the mode propagating along the photonic crystal waveguide structure passes through the medium, and the resulting interactions with the medium can alter the propagation speed and/or attenuation of the evanescent tail. In this example, the thickness of the overclad layer 514 (of the laser 502) can also be adjusted to provide a receptacle for the medium, to accommodate the refractive indices of various combinations of core and cladding materials, etc. In this example embodiment, voids 516 are arranged in a pattern that provides the photonic crystal double pass interferometer structure 504. Thus, interaction between the evanescent field and the medium in the sensed medium region 512 effects the characteristics of the light (denoted by arrow 518) reflected by the photonic crystal double pass interferometer structure 504, thereby providing an output indicative of the sensed medium.

Figure 6:
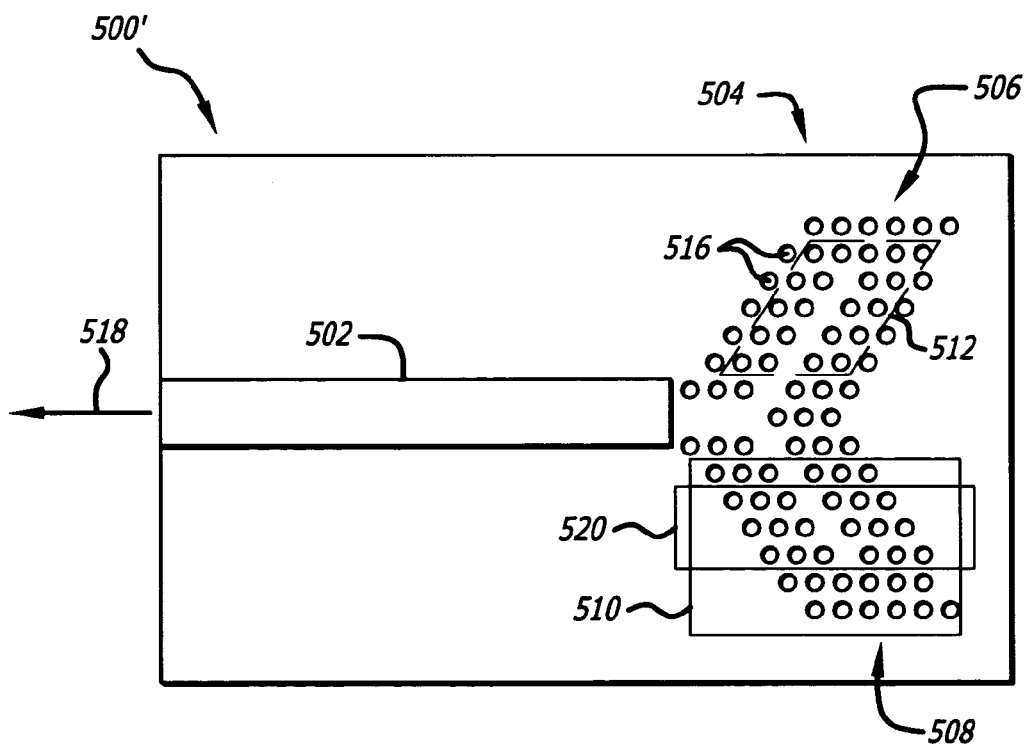
FIG. 6 is a top view of the laser sensor apparatus with a photonic crystal double pass interferometer of FIG. 5 provided with a phase shifter.

Referring to FIG. 6, in another embodiment, the reference arm 508 of an otherwise identical laser sensor apparatus 500' is provided with a phase shifter 520 for adjusting the operating point of the laser at an optimal or desired sensitivity point for detection (e.g., of a particular type or species of medium). The phase shifter 520 can also be used for biasing out manufacturing defects, compensating for contamination, and resetting the laser sensor apparatus 500' to a new operating point. Phase shifting can be accomplished in semiconductors by carrier injection which changes the refractive index of the semiconductor locally. Carrier injection can be either electrical using pn junctions or metal semiconductor junctions or optical pumping by injecting electrons and holes of a local region.

Figure 7:
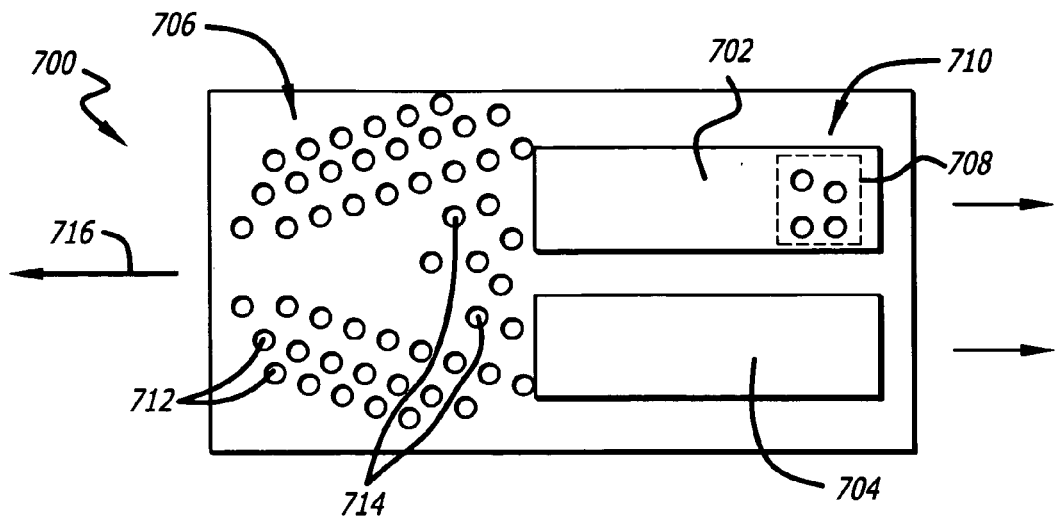
FIG. 7 is a top view of an example photonic crystal waveguide configured for combining the outputs of a sensor laser and a reference laser.

Other sensor apparatuses include photonic crystal waveguide combiner structures. By way of example, and referring to FIG. 7, a laser sensor apparatus 700 includes a sensor laser 702 and a reference laser 704 (e.g., semiconductor lasers) and a photonic crystal heterodyning structure 706 which is optically coupled to the sensor laser 702 and the reference laser 704 as shown. The sensor laser 702 is also provided with a sensed medium region 708 (shown in dashed lines) which is positioned over a photonic crystal structure 710 of the sensor laser 702. In operation, a chemical, biological or other medium is placed in the sensed medium region 708. The evanescent field resulting from light propagating along the photonic crystal structure 710 "probes" the medium. More specifically, the evanescent tail of the mode propagating along the photonic crystal structure 710 passes through the medium, and the resulting interactions with the medium can alter the propagation speed and/or attenuation of the evanescent tail. In this example embodiment, voids 712 are arranged in a pattern that provides the photonic crystal heterodyning structure 706 (which combines the light outputs of the sensor laser 702 and the reference laser 704). In this example, the photonic crystal heterodyning structure 706 includes photonic crystal partial mirrors 714 adjacent to the sensor laser 702 and the reference laser 704 as shown. Thus, interaction between the evanescent field and the medium in the sensed medium region 708 effects the characteristics of the light (denoted by arrow 716) output by the photonic crystal heterodyning structure 706, thereby providing an output indicative of the sensed medium.

Figure 8:
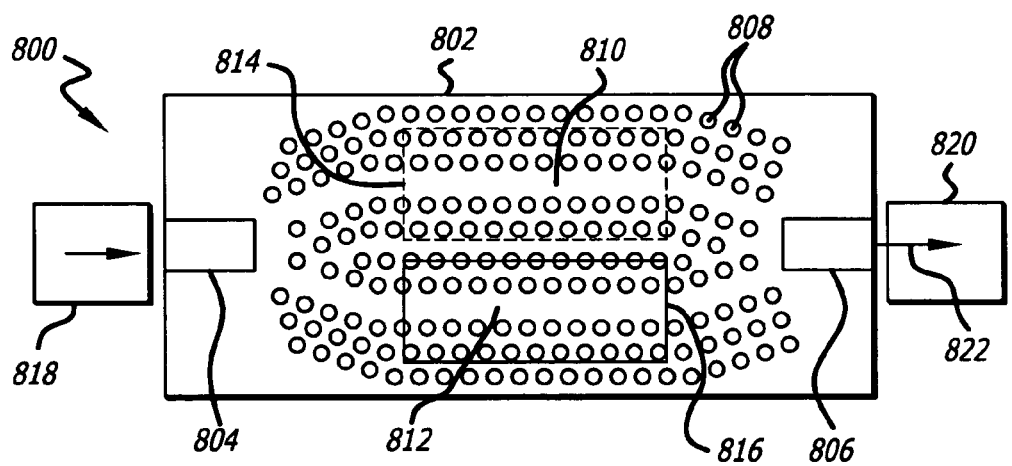
FIG. 8 is a top view of an example Mach Zehnder planar photonic crystal waveguide sensor.

Photonic crystal structures as described herein can also be used to provide passive sensor apparatuses. By way of example, and referring to FIG. 8, a Mach Zehnder planar photonic crystal waveguide sensor 800 includes a photonic crystal Mach Zehnder interferometer structure 802 and conventional waveguide-to-photonic crystal transition elements 804 and 806 which are optically coupled as shown to the input and the output of the photonic crystal Mach Zehnder interferometer structure 802, respectively. In this example embodiment, the photonic crystal Mach Zehnder interferometer structure 802 includes voids 808 arranged in a pattern defining a sensor waveguide arm 810 and a reference waveguide arm 812 as shown. The photonic crystal Mach Zehnder interferometer structure 802 is also provided with a sensed medium region 814 (shown in dashed lines) positioned over the sensor waveguide arm 810. In this example, the reference waveguide arm 812 is provided with a phase shifter 816 for biasing out manufacturing defects, compensating for contamination, and resetting the Mach Zehnder planar photonic crystal waveguide sensor 800 to a new operating point. Another method of phase shifting in addition to carrier injection either optically or electrically is to apply a DC bias and use the electro-optic effect in III-V semiconductors. A field is applied via a metal semiconductor or metal oxide semiconductor contact to the semiconducting region. In this example, optical fibers 818 and 820 are optically coupled to the transition elements 804 and 806, respectively. In operation, a chemical, biological or other medium is placed in the sensed medium region 814. The evanescent field resulting from light propagating along the sensor waveguide arm 810 "probes" the medium. More specifically, the evanescent tail of the mode propagating along the sensor waveguide arm 810 passes through the medium, and the resulting interactions with the medium can alter the propagation speed and/or attenuation of the evanescent tail. By varying the optical path length of the sensor waveguide arm 810, the difference in optical path length between the sensor waveguide arm 810 and the reference waveguide arm 812 controls the interference of the optical signals propagating in those waveguides upon recombination. Thus, interaction between the evanescent field and the medium in the sensed medium region 814 effects the characteristics of the light (denoted by arrow 822) output by the photonic crystal Mach Zehnder interferometer structure 802, thereby providing an output indicative of the sensed medium.

Figure 9:
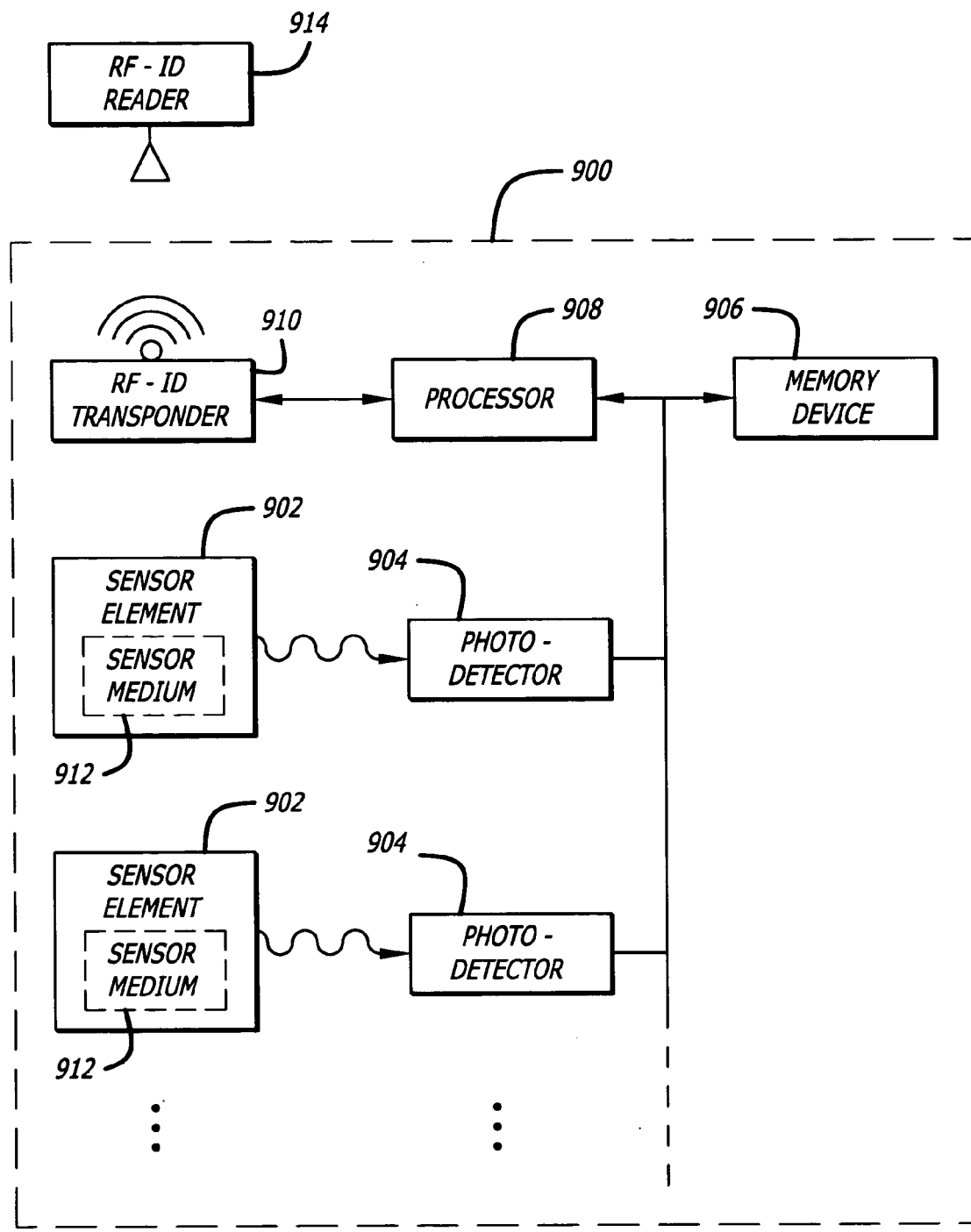
FIG. 9 is a diagram of an example sensor apparatus with multiple sensor elements.

Sensor apparatuses including multiple sensor elements can also be provided. By way of example, and referring to FIG. 9, a sensor apparatus 900 (shown in dashed lines) includes multiple sensor elements 902, multiple photodetectors 904, a memory device 906, a processor 908 and a transponder 910, configured as shown. Each of the sensor elements 902 is configured to operatively interface with a sample of sensed medium 912 (shown in dashed lines) as, for example, with the previously described sensors. For example, each of the sensor elements 902 can be a laser sensor apparatus with a photonic crystal structure that defines a mirror, a double pass interferometer, or a combiner, or a passive sensor apparatus with a photonic crystal Mach Zehnder interferometer or other photonic crystal structure. In operation, outputs of the sensor elements 902 are detected by their corresponding photodectors 904, which convert the detected light outputs to data signals that are provided to the memory device 906 and/or processor 908. By way of example, a signal analysis computer-executable program and characteristic information associated with various media are stored in the memory device 906. The data signals are received and processed by the processor 908 which executes the signal analysis program to provide processed data to the transponder 910 for transmission. Alternatively, the signal analysis functionality can be implemented "off sensor". In an example embodiment, the transponder 910 is a radio frequency identification (RF-ID) transponder configured to transmit data corresponding to the outputs of the sensor elements 902 in response to a sensor interrogation signal. As illustrated in this example embodiment, such an interrogation signal can be provided by a RF-ID reader 914.

Although the present invention has been described in terms of the example embodiments above, numerous modifications and/or additions to the above-described embodiments would be readily apparent to one skilled in the art. It is intended that the scope of the present invention extends to all such modifications and/or additions.

We claim:

1. A sensor apparatus comprising:
   a photonic crystal structure including a Mach Zehnder interferometer with a reference arm and a sensor arm configured to provide an evanescent field through a sensed medium region adjacent to the sensor arm, the sensed medium region being part of the photonic crystal structure.

2. The sensor apparatus of claim 1, wherein the Mach Zehnder interferometer is passive.

3. The sensor apparatus of claim 1, wherein the sensed medium region is configured to receive a chemical or biological medium.

4. The sensor apparatus of claim 1, further comprising:
   a phase shifter for the reference arm.

5. The sensor apparatus of claim 1, further comprising:
   means for optically coupling the photonic crystal structure to an optical fiber.

6. The sensor apparatus of claim 1, wherein the photonic crystal structure is formed from III-V semiconductor materials.

7. The sensor apparatus of claim 1, wherein the photonic crystal structure includes defects formed by nanoimprinting a pattern and etching the pattern.

8. A sensor apparatus comprising:
   multiple sensor elements, each of the sensor elements including a photonic crystal Mach Zehnder interferometer with a reference arm and a sensor arm configured to provide an evanescent field through a sensed medium region adjacent to the sensor arm, each of the sensed medium regions being part of a photonic crystal structure of the photonic crystal Mach Zehnder interferometer; and
   mechanism for detecting outputs of the multiple sensor elements and converting the outputs into data.

9. The sensor apparatus of claim 8, wherein the means for detecting includes a photodetector.

10. The sensor apparatus of claim 8, further comprising:
    means for processing the data to identify articles of media provided to the sensed medium regions.

11. The sensor apparatus of claim 8, further comprising:
    means for transmitting the data.

12. The sensor apparatus of claim 8, further comprising:
    means for transmitting the data in response to an interrogation signal received by the sensor apparatus.

13. The sensor apparatus of claim 12, wherein the means for transmitting includes a radio-frequency identification (RE-ID) transponder.

14. The sensor apparatus of claim 8, wherein one or more of the photonic crystal Mach Zehnder interferometers is formed from III-V semiconductor materials.

15. The sensor apparatus of claim 8, wherein one or more of the photonic crystal Mach Zehnder interferometers includes defects formed by nanoimprinting a pattern and etching the pattern.

16. A method for sensing comprising:
    providing a photonic crystal Mach Zehnder interferometer that generates an evanescent field through a sensed medium region which is part of a photonic crystal structure of the photonic crystal Mach Zehnder interferometer;
    providing an article of medium at the sensed medium region;
    optically coupling a light source to an input of the photonic crystal Mach Zehnder interferometer; and
    detecting an output of the photonic crystal Mach Zehnder interferometer.

17. The method for sensing of claim 16, wherein the article of medium is a chemical or biological medium.

18. The method for sensing of claim 16, further comprising:
    processing data corresponding to the output.

19. The method for sensing of claim 16, further comprising:
    processing data corresponding to the output to identify the article of medium.

20. The method for sensing of claim 16, further comprising:
    transmitting data corresponding to the output.

21. The method for sensing of claim 16, further comprising:
    transmitting data corresponding to the output in response to a sensor interrogation signal.

* * * * *

UNITED STATES PATENT AND TRADEMARK OFFICE
CERTIFICATE OF CORRECTION

PATENT NO. : 7,289,221 B2  Page 1 of 1
APPLICATION NO. : 10/951918
DATED : October 30, 2007
INVENTOR(S) : Shih-Yuan Wang et al.

It is certified that error appears in the above-identified patent and that said Letters Patent is hereby corrected as shown below:

In column 8, line 6, in Claim 13, delete "(RE-ID)" and insert -- (RF-ID) --, therefor.

Signed and Sealed this

Fourteenth Day of July, 2009

JOHN DOLL
*Acting Director of the United States Patent and Trademark Office*